(12) United States Patent
Janin

(10) Patent No.: US 11,324,752 B2
(45) Date of Patent: May 10, 2022

(54) IMEGLIMIN FOR PREVENTING AND/OR TREATING HEPATOCELLULAR CARCINOMA

(71) Applicant: Eric Janin, Toulouse (FR)

(72) Inventor: Eric Janin, Toulouse (FR)

(73) Assignee: ERICARE, Toulouse (FR)

( * ) Notice: Subject to any disclaimer, the term of this patent is extended or adjusted under 35 U.S.C. 154(b) by 149 days.

(21) Appl. No.: 16/627,326

(22) PCT Filed: Jul. 4, 2018

(86) PCT No.: PCT/FR2018/000188
§ 371 (c)(1),
(2) Date: Dec. 29, 2019

(87) PCT Pub. No.: WO2019/008239
PCT Pub. Date: Jan. 10, 2019

(65) Prior Publication Data
US 2020/0163971 A1    May 28, 2020

(30) Foreign Application Priority Data

Jul. 5, 2017 (FR) .......................... 1700713

(51) Int. Cl.
*A61K 31/53* (2006.01)
*A61P 35/00* (2006.01)
*A61K 31/44* (2006.01)

(52) U.S. Cl.
CPC .............. *A61K 31/53* (2013.01); *A61K 31/44* (2013.01); *A61P 35/00* (2018.01)

(58) Field of Classification Search
CPC ..................................................... A61K 31/53
See application file for complete search history.

(56) References Cited

U.S. PATENT DOCUMENTS

2003/0109530 A1   6/2003  Lipha
2011/0236317 A1   9/2011  Poxel

FOREIGN PATENT DOCUMENTS

WO   WO2011006983        1/2011
WO   WO-2014107617 A1 *  7/2014  .......... A61K 9/2846

OTHER PUBLICATIONS

Cauchy, et al., "Strong Antineoplastic Effects of Metformin in Preclinical Models of Liver Carcinogenesis," Clinical Science, vol. 131, No. 1, Nov. 1, 2016, pp. 27-36.
Sunbin Ling, et al., "Metformin Reverses Multidrug Resistance in Human Hepatocellular Carcinoma," Molecular Medicine Reports, vol. 10, No. 6, Oct. 8, 2014.
V. Pirags, et al., "Imeglimin, a Novel Glimin Oral Antidiabetic, Exhibits a Good Efficacy and Safety Profile . . . ," Diabetes, Obesity and Metabolism, vol. 14, No. 9, May 2012.
Swamy, et al., "Targeting Multiple Oncogenic Pathways for the Treatment of Hepatocellular Carcinoma," Targeted Oncology, vol. 12, No. 1, Aug. 2016.
Bruix Jordi, et al., Evidence-Based Diagnosis, Staging and Treatment of Patients with Hepatocellular Carcinoma, Gastroenterology, W.B. Saunders Co., vol. 150, No. 4, Jan. 2016.

* cited by examiner

*Primary Examiner* — John S Kenyon
(74) *Attorney, Agent, or Firm* — CRGO Global; Steven M. Greenberg

(57) ABSTRACT

Use of imeglimin for the prevention and/or treatment of hepatocellular carcinoma.

9 Claims, 1 Drawing Sheet

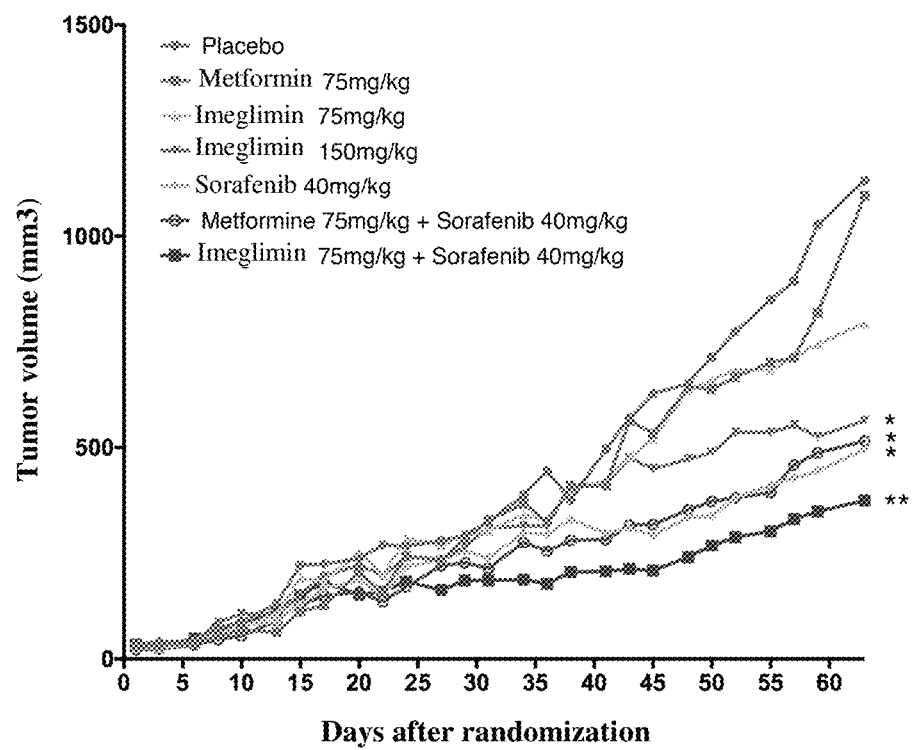
Evolution subject to treatment of tumor volumes (in vivo study)

IMEGLIMIN FOR PREVENTING AND/OR TREATING HEPATOCELLULAR CARCINOMA

CROSS-REFERENCE TO RELATED APPLICATIONS

This application is a § 371 national phase entry of International Application No. PCT/FR2018/000188, filed Jul. 4, 2018, which claims priority to French Patent Application No. 1700713, filed Jul. 5, 2017.

The present invention relates to the use of imeglimin or ((6R)-(+)-4-dimethylamino-2-imino-6-methyl-1,2,5,6-tetra-hydro-1,3,5-triazine hydrochloride) of formula (I):

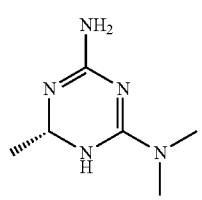

for the prevention and/or treatment of hepatocellular carcinoma.

Liver cancers worldwide represent over 850,000 new cases per year, 90% of which are hepatocellular carcinoma cases. Hepatocellular carcinoma is the third leading cause of cancer death in the world.

Chronic infection with the hepatitis C virus (HCV) or the hepatitis B virus (HBV) is the leading cause of hepatocellular carcinoma (Nat Rev Dis Primers 2016, 2: 16018).

The incidence of hepatocellular carcinoma is higher in type 2 diabetics than in non-diabetics, whether or not these patients also have liver disease (Curr Diab Rep 2017, 17: 20).

The treatment of hepatocellular carcinoma is essential since it may be fatal. Current curative treatments are surgery with tumor resection and/or liver transplantation. However, when the diagnosis is late and the disease is discovered at an advanced stage, these treatments are no longer possible. The standard treatment at this advanced stage is sorafenib, an active small molecule administered orally, a multikinase inhibitor and an anti-angiogenic. In these patients, the median survival time is 10.7 months in those treated with sorafenib and 7.9 months in those receiving a placebo. Diarrhea, weight loss, hand-foot syndrome and hypophosphatemia are the most important side effects in the sorafenib group (New England Journal of Medicine 2008, 359: 378-90).

Metformin, a biguanide normoglycemic agent, is an oral anti-diabetic agent that decreases hepatic glucose production. It is the standard treatment of type 2 diabetes, the most prescribed first-line treatment.

Inhibition of the mitochondrial I complex and activation of AMP-activated protein kinase (AMPK) are involved in the effects of metformin (Cell Metabolism 2014, 20: 953-66).

Epidemiological, retrospective or cohort studies show that metformin-treated patients with type 2 diabetes have fewer cancers than diabetics treated with other anti-diabetic drugs (Diabetes Care 2009, 9: 1620-25, BMC Cancer 2011, 11:20; Gut 2013, 62: 606-15) and in particular in hepatocellular carcinoma (Am J Gastroenterol 2013, 108: 881-91).

Experimental studies have also shown that metformin had innate anti-tumor properties. In hepatocellular carcinoma, in vitro, metformin has cell growth inhibitory activity on HepG2 and HuH7 lines. In vivo, in subcutaneous heterograft models of human liver tumor cells, in immunocompromised mice, metformin exhibits anti-cancer activity. Clinical studies are underway to confirm the activity of metformin in combination with anti-cancer drugs in different cancers. (Gut 2013, 62: 606-15; J Hematol Oncol 2016, 9:20).

Imeglimin is a tetrahydrotriazine, the first representative of a new chemical class of oral anti-diabetic agents, the glimins.

Unlike metformin, imeglimin does not inhibit mitochondrial I complex.

Imeglimin acts simultaneously on the three main organs directly involved in glucose homeostasis: the liver, muscles and pancreas.

Imeglimin inhibits hepatic glucose production. It improves the sensitivity of organs to glucose and insulin. It restores insulin secretion in response to glucose.

In the STZ diabetic rat, after 35 days of treatment, imeglimin significantly decreased fasting blood glucose and HbA1c for doses of 50 and 100 mg/kg/day. These effects are similar to those of metformin at 50 mg/kg/day (Cell Death Discovery 2016; 2: 15072; J Diabetes Metab 2011, 2: 4).

Out of seven Phase 1 studies that were conducted, exposing a total of 216 subjects to imeglimin, the product exhibited excellent administration safety and tolerance, with a comparable number of adverse effects between subjects who received a placebo and those who received imeglimin.

Out of seven Phase 2 studies that were conducted, exposing 611 patients to imeglimin, the efficacy of the product was evaluated using glycemic parameters and certain non-glycemic parameters. Similarly, the tolerance and safety of use were evaluated. Imeglimin exhibited excellent tolerance and safety of use similar to those of the placebo.

Two Phase 2a clinical studies demonstrated that 1500 mg of imeglimin, administered twice daily, improves hemoglobin A1c and fasting glucose levels in a manner similar to 850 mg of metformin, administered twice daily. These studies show a tolerance profile of imeglimin that is greater than that of metformin in diabetic patients. In Europe, the United States and Japan, imeglimin is at the end of Phase 2 clinical development in type 2 diabetes (www.poxel.com/Poxel-Imeglimin-fact-sheet_en.pdf; Drugs R D 2015, 15: 227-32).

Imeglimin is protected by the family of patents derived from WO2001/0155122 (applicant Lipha).

The patent covers a Markush formula including imeglimin, as well as a method of preparation, the pharmaceutical compositions and the use in the treatment of pathologies associated with insulin resistance syndrome, more particularly diabetes, the pathologies caused by the formation of glycosylation products, dyslipidemia, obesity, high blood pressure, retinopathies and neuropathies, renal complications, atherosclerosis, angiopathy, Alzheimer's disease, neurodegenerative diseases, senility.

The Applicant has now discovered that imeglimin possesses outstanding, unexpected pharmacological properties in relation to cancer, more particularly in relation to hepatocellular carcinoma.

In the tests carried out, imeglimin was compared with metformin, the reference anti-diabetic drug.

Imeglimin demonstrates, in vitro, a cell proliferation inhibitory potential that is two to four times greater than that of metformin in two human tumor cell lines of primary liver cancer (HepG2 and HuH7).

In addition, imeglimin demonstrates, in vivo, on subcutaneous xenograft models of the HepG2 line in 6 week old female mice with a BALB/c nude genetic background (Harlan), a dose-dependent inhibitory effect on tumor growth, not significantly different from sorafenib and higher than metformin. In addition, imeglimin potentiates the activity of sorafenib, the standard medical treatment for hepatocellular carcinoma, to a greater extent than sorafenib-associated metformin. Imeglimin thus proves to be a very interesting therapeutic application in the prevention and/or treatment of cancer, more particularly of hepatocellular carcinoma.

The anti-tumor efficacy of imeglimin, combined with its excellent tolerance, fulfills a real, unmet medical need in the treatment of cancers.

The invention relates to imeglimin for its use in pharmaceutical compositions intended for the curative and/or preventive treatment of cancer, more particularly of hepatocellular carcinoma, administered alone or in combination with anti-cancer agents such as kinase inhibitors, and more particularly sorafenib and regorafenib, immune checkpoint inhibitors, and more specifically nivolumab. Moreover, the combination administration can be in the form of a simultaneous or successive co-administration of two separate pharmaceutical compositions, each containing one of the active ingredients (free association), or in the form of the administration of a fixed combination of the two active ingredients within the same pharmaceutical composition.

The pharmaceutical compositions will be presented in forms suitable for oral, parenteral, transcutaneous, nasal, rectal, perlingual administration, and especially in the form of injectable preparations, sublingual tablets, tablets, gel capsules, capsules, tablets, suppositories, creams, ointments, dermal gels, etc.

The corresponding pharmaceutical compositions can allow instantaneous or delayed release of the active ingredient.

In addition to imeglimin, the pharmaceutical compositions according to the invention contain one or more excipients or vehicles selected from diluents, lubricants, binders, disintegrating agents, absorbents, colorants, sweeteners, etc.

By way of example, and in a non-limiting manner, the following can be cited:
- for the diluents: lactose, dextrose, sucrose, mannitol, sorbitol, cellulose, glycerin;
- for the lubricants: silica, talc, stearic acid and magnesium and calcium salts, polyethylene glycol;
- for the binders: aluminum and magnesium silicate, starch, gelatin, tragacanth, methylcellulose, sodium carboxymethylcellulose and polyvinylpyrrolidone;
- for the disintegrating agents: agar, alginic acid and its sodium salt, effervescent mixtures.

The dosing regimen varies according to the sex, the age and the weight of the patient, the route of administration, the nature of the disease and of possibly associated treatments, and ranges between 25 mg and 6 g of imeglimin per 24 hours, for example, between 500 mg to 4 g per day.

Preferably, the daily dose of imeglimin will be 3 g per day.

The following examples illustrate the invention.

FIG. 1 is a two-dimensional graph illustrating a graphical relationship between a tumor volume and days after randomization.

Pharmacological Study

EXAMPLE 1

In vitro anti-proliferative effect of imeglimin compared to that of metformin in 2 models of human hepatocellular carcinoma (HCC). Determination of IC50 (median inhibitory concentration) by the MTS Promega™ cell proliferation assay (CellTiter 96™ AQueous Nonradioactive Cell Proliferation Assay Kit).

A) Protocol:

Different mM concentrations (0, 0.1, 0.25, 0.5, 1.0, 2.5, 5.0, 7.5, 10, 25, 50, 100) of imeglimin and metformin were tested in vitro on two human CHC cell lines, HepG2 and HuH7, over a period of 6 days.

B) Results:

The inhibitory effect of imeglimin on cell proliferation of HepG2 and HuH7 lines is 2 to 4 times greater than that of metformin for concentrations of 2.5 to 25 mM. The effect of imeglimin is much more marked on the HuH7 line.

The inhibitory effect increases with time for imeglimin.

The IC50 values of metformin are higher than those of imeglimin by at least a factor of 2. This ratio increases with the treatment time, up to 6 for HuH7.

EXAMPLE 2

In vivo anti-tumor activity of imeglimin compared to that of metformin, alone or in combination with sorafenib, on subcutaneous xenograft models of the CHC HepG2 line in 6 week old female mice with a BALB/c nude genetic background (Harlan).

A) Protocol:

Two million cells of the HepG2 line are injected into the left side of each mouse in a volume of 100 µl (50 µl PBS-50 µl matrigel). Mice developing a palpable tumor are randomized into 7 groups of
treatment of 14 mice according to the following design: placebo, imeglimin 75 mg/kg/day, imeglimin 150 mg/kg/day, metformin 75 mg/kg/day, sorafenib 40 mg/kg/day, imeglimin 75 mg/kg/day+sorafenib 40 mg/kg/day, metformin 75 mg/kg/day+sorafenib 40 mg/kg/day.

Metformin and imeglimin are administered in drinking water, sorafenib is administered by oral gavage. Treatment begins on the day of randomization.

Metformin doses of 75 mg/kg/day and imeglimin of 150 mg/kg/day used in this in vivo animal study correspond to equipotent doses in diabetics.

The treatments were administered for 63 days. The evolution curves of the tumor volumes, as well as those of the weight of the animals, were analyzed during this period. The appearance of tumors and organs has been the subject of a macroscopic anatomic-pathological analysis.

B) Results

Imeglimin, metformin and sorafenib slow down the growth in volume of grafted tumors in mice compared to the placebo control group (see FIG. 1/1).

For equipotent doses, the effect on tumor volume of imeglimin at 150 mg/kg/day is significantly greater than that of metformin at 75 mg/kg/day compared with the placebo.

The efficacy of imeglimin increases with the doubling of doses from 75 mg/kg/day to 150 mg/kg/day (dose effect).

Treatment with imeglimin at 150 mg/kg/day does not have a significantly different effect from that of sorafenib at 40 mg/kg/day.

An additional effect on volume is noted when imeglimin at 75 mg/kg/day is associated with sorafenib at 40 mg/kg/day. In addition, this activity is significantly greater than that of metformin at 75 mg/kg/day associated with sorafenib at 40 mg/kg/day.

From an observational point of view, at the time of sacrifice of the mice, it is noted that if sorafenib 40 mg/kg/day alone exerts its anti-angiogenic properties, the imeglimin combination at 75 mg/kg/day, plus sorafenib at 40 mg/kg/day, enhances the anti-angiogenic effects of sorafenib.

The treatment with imeglimin did not prove to be toxic, the mean weight of the animals did not change during the 63 days of treatment.

EXAMPLE 3: PHARMACEUTICAL COMPOSITIONS

Formulation 1:
Imeglimin: 1000 mg
Microcrystalline cellulose: 150 mg
Croscarmellose: 25 mg
Polyvinylpyrrolidone: 45 mg
Magnesium stearate: 10 mg
Eudragit®: 25 mg
Formulation 2:
Imeglimin: 750 mg
Sorafenib: 200 mg
Microcrystalline cellulose: 110 mg
Croscarmellose: 21 mg
Polyvinylpyrrolidone: 30 mg
Magnesium stearate: 10.5 mg
Opadry®: 20 mg

The invention claimed is:

1. Pharmaceutical compositions containing imeglimin and a second active ingredient used in the treatment of hepatocellular carcinoma in combination with one or more inert, non-toxic and pharmaceutically acceptable excipients or vehicles wherein the second active ingredient is sorafenib.

2. Association of imeglimin and of sorafenib to use in the prevention and/or treatment of hepatocellular carcinoma.

3. A method of treating and/or preventing hepatocellular carcinoma in a subject, comprising administering to the subject a therapeutically effective amount of imeglimin.

4. The method according to claim 3, wherein it further comprises administering to the subject a therapeutically effective amount of a second active ingredient.

5. The method according to claim 4, wherein said second active ingredient is a kinase inhibitor.

6. The method according to claim 5, wherein said kinase inhibitor is sorafenib.

7. The method according to claim 5, wherein said kinase inhibitor is regorafenib.

8. The method according to claim 4, wherein said second active ingredient is an immune checkpoint inhibitor.

9. The method according to claim 3, wherein the dosing regimen of said imeglimin ranges between 25 mg and 6 g of imeglimin per 24 hours.

* * * * *